(12) United States Patent
Mitchell et al.

(10) Patent No.: US 10,725,197 B2
(45) Date of Patent: Jul. 28, 2020

(54) METHODS FOR INTERPRETING NMR DATA

(71) Applicant: SCHLUMBERGER TECHNOLOGY CORPORATION, Sugar Land, TX (US)

(72) Inventors: Jonathan Mitchell, Cambridge (GB); Edmund J. Fordham, Cambridge (GB); Lukasz Zielinski, Cambridge (GB); Ravinath Kausik Kadayam Viswanathan, Cambridge (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 250 days.

(21) Appl. No.: 15/695,727

(22) Filed: Sep. 5, 2017

(65) Prior Publication Data

US 2018/0203153 A1    Jul. 19, 2018

Related U.S. Application Data

(60) Provisional application No. 62/383,242, filed on Sep. 2, 2016.

(51) Int. Cl.
*G01V 3/32* (2006.01)
*G01V 3/38* (2006.01)
(Continued)

(52) U.S. Cl.
CPC ............... *G01V 3/32* (2013.01); *G01V 3/38* (2013.01); *E21B 49/00* (2013.01); *G01N 33/24* (2013.01); *Y02A 90/344* (2018.01)

(58) Field of Classification Search
CPC .................................. G01V 3/32; G01V 3/38
See application file for complete search history.

(56) References Cited

U.S. PATENT DOCUMENTS 6,201,392 B1    3/2001   Anderson et al.
6,759,601 B1 *  7/2004   Petty .................... G01N 24/085
                                                      177/1
(Continued)

OTHER PUBLICATIONS

Akpa, B. S. et al., "Enhanced 13C PFG NMR for the study of hydrodynamic dispersion in porous media", Journal of Magnetic Resonance, 2007, 186(1), pp. 160-165.
(Continued)

*Primary Examiner* — Dixomara Vargas

(57) ABSTRACT

Methods for improved interpretation of NMR data acquired from industrial samples by simultaneously detecting more than one resonant nucleus without removing the sample from the sensitive volume of the NMR magnet or radio frequency probe are disclosed. In other aspects, the present disclosure provides methods for robust imaging/analysis of spatial distribution of different fluids (e.g., 1H, 23Na, 19F) within a core or reservoir rock. NMR data may be interpreted in real-time during dynamic processes to enable rapid screening, e.g. of enhanced oil recovery techniques and products and/or to provide improved interpretation of well-logs. Measurements of resonant nuclei other than 1H may be performed in the laboratory or downhole with a NMR logging tool. In other aspects, the present disclosure describes a novel kernel function to extract values for underlying parameters that define relaxation time behavior of a quadrupolar nucleus.

20 Claims, 12 Drawing Sheets

(51) Int. Cl.
G01N 33/24 (2006.01)
E21B 49/00 (2006.01)

(56) References Cited

U.S. PATENT DOCUMENTS

| | | | |
|---|---|---|---|
| 8,115,481 B2 | 2/2012 | Chen | |
| 9,696,269 B2 | 7/2017 | Fordham et al. | |
| 2003/0210050 A1* | 11/2003 | Prammer | G01V 3/32 324/315 |
| 2004/0231699 A1* | 11/2004 | Corver | B03C 1/22 134/3 |
| 2004/0251904 A1* | 12/2004 | Corver | G01N 24/08 324/321 |
| 2005/0116712 A1* | 6/2005 | Corver | G01N 24/08 324/309 |
| 2005/0122104 A1* | 6/2005 | Corver | G01N 24/08 324/309 |
| 2005/0242808 A1* | 11/2005 | McKendry | G01N 24/085 324/307 |
| 2005/0242809 A1* | 11/2005 | McKendry | G01G 9/005 324/308 |
| 2005/0242811 A1* | 11/2005 | Schaepman | G01K 7/42 324/315 |
| 2005/0242813 A1* | 11/2005 | Aptaker | G01N 24/085 324/318 |
| 2005/0247493 A1* | 11/2005 | Aptaker | G01G 9/00 177/1 |
| 2009/0179636 A1 | 7/2009 | Chen | |
| 2013/0234706 A1 | 9/2013 | Mandal et al. | |
| 2013/0311110 A1* | 11/2013 | Aizikov | H01J 49/0036 702/32 |
| 2013/0325348 A1 | 12/2013 | Valori et al. | |
| 2014/0341455 A1 | 11/2014 | Cao | |
| 2015/0077111 A1 | 3/2015 | Rudakov et al. | |
| 2015/0192011 A1 | 7/2015 | Mandal et al. | |

OTHER PUBLICATIONS

Allen, D. F. et al., "How to use borehole nuclear magnetic resonance", Schlumberger Oil Review, 1997, 9, pp. 34-57.
Allen, D. F. et al., "Trends in NMR Logging", Schlumberger Oilfield Review, 2000, 12, pp. 2-19.
Amott, E., "Observations Relating to the Wettability of Porous Media", Petroleum Transactions AIME, 1959, 216, pp. 156-162.
Archie, G. E., "The Electrical Resistivity Log as an Aid in Determining Some Reservoir Characteristics", Transactions of the AIME, 1942, 146(1), pp. 54-62.
Arora, S. et al., "Single-well In-situ Measurement of Risidual Oil Saturation after an EOR Chemical Flood", SPE 129069 presented at the SPE EOR Conference at Oil and Gas West Asia, Muscat, Oman, 2010, 18 pages.
Bedford, R. G. et al., "Solubilities and Volume Changes Attending Mixing for the System: Perfluoro-n-Hexane-n-Hexane", Journal of the American Chemical Society, 1958, 80(2), pp. 282-285.
Bijeljic, B. et al., "Signature of Non-Fickian Solute Transport in Complex Heterogeneous Porous Media", Physical Review Letters, 2011, 107, pp. 204502: 4 pages.
Borgia, G. C. et al., "Developments in Core Analysis by NMR Measurements", Magnetic Resonance Imaging, 1996, 14(7-8), pp. 751-760.
Brancolini, A. et al., "The Use of NMR Core Analysis in the Interpretation of Downhole NMR Logs", SPE 30559 presented at the Annual Technical Conference and Exhibition, Dallas, Texas, USA, 1995, 10 pages.
Brown, J. A. et al., "NMR Logging Tool Development: Laboratory Studies of Tight Gas Sands and Artificial Porous Material", SPE 10813 presented at the SPE/DOE Unconventional Gas Recovery Symposium, Pittsburgh, Pennsylvania, USA, 1982, pp. 203-208.
Brown, R. J. S. et al., "Measurements of Fractional Wettability of Oilfield Rocks by the Nuclear Magnetic Relaxation Method", Fall Meeting of the Petroleum Branch of AIME, Los Angeles, California, 1956, pp. 1-4.

Brownstein, K. R., et al., "Spin-Lattice Relaxation in a System Governed by Diffusion", Journal of Magnetic Resonance, 1977, 26(1), pp. 17-24.
Bryan, J. et al., "Measurement of Emulsion Flow in Porous Media: Improvements in Heavy Oil Recovery", Journal of Physics: Conference Series 147, 2009, 012058, 16 pages.
Cense, A. W., "How Reliable is In Situ Saturation Monitoring (ISSM) using X-ray?", SCA2014-009 presented at the International Symposium of the Society of Core Analysts held in Avignon, France, 2014, 12 pages.
Chen, J. et al., "NMR wettability indices: Effect of OBM on wettability and NMR responses", Journal of Petroleum Sciences and Engineering, 2006, 52, pp. 161-171.
Chen, Q. et al., "Measurement of rock-core capillary pressure curves using a single-speed centrifuge and one-dimensional magnetic-resonance imaging", Journal of Chemical Physics, 2005, 122, 214720, 8 pages.
Choi, C. H. et al., "Design and construction of an actively frequency-switchable RF coil for field-dependent Magnetisation Transfer Contrast MRI with fast field-cycling", Journal of Magnetic Resonance, 2010, 207(1), pp. 134-139.
Clarke, A., et al., "Mechanism of anomalously increased oil displacement with aqueous viscoelastic polymer solutions", Soft Matter, 2015, 11, pp. 3536-3541.
Creber, S. A., et al., "Quantification of the velocity acceleration factor for colloidal transport in porous media using NMR", Journal of Colloid and Interface Science, 2009, 339(1), pp. 168-174.
Damion, R. A. et al., "Pore-scale network modelling of flow propagators derived from pulsed magnetic field gradient spin echo NMR measurements in porous media", Chemical Engineering Science, 2000, 55, pp. 5981-5998.
Donaldson, E. C., et al., "Wettability determination and its effect on recovery efficiency", Society of Petroleum Engineers Journal, 1969, 9(1), pp. 13-20.
Flaum, M. et al., "NMR Diffusion Editing for D-T2 Maps: Application to Recognition of Wettability Change", Petrophysics, 2005, 46(2), pp. 113-123.
Fleury, M. et al., "Quantitative analysis of diffusional pore coupling from T2-store-T2 NMR experiments", Journal of Colloid and Interface Science, 2009, 336(1), pp. 250-259.
Forbes, P. "Simple and Accurate Methods for Converting Centrifuge Data Into Drainage and Imbibition Capillary Pressure Curves", The Log Analyst, 1994, 35(4), pp. 31-53.
Freedman, R., "Advances in NMR Logging", Journal of Petroleum Technology, 2006, 58(1), pp. 60-66.
Freedman, R., et al., "Fluid Characterization using Nuclear Magnetic Resonance Logging", Petrophysics, 2004, 45(3), pp. 241-250.
Goelman, G. et al., "The CPMG Pulse Sequence in Strong Magnetic Field Gradients with Applications to Oil-Well Logging", Journal of Magnetic Resonance, Series A, 1995, 113(1), pp. 11-18.
Hassler, G. L. et al., "Measurement of capillary pressures in small samples", Transactions of the AIME, 1945, 160(1), pp. 114-123.
Headley, L. C. et al., "Nuclear magnetic resonance relaxation of lithium ions in water solutions in porous materials", Journal of Magnetic Resonance (1969), 1971, 5(2), pp. 168-173.
Headley, L. C., "Nuclear magnetic resonance relaxation of 23Na in porous media containing NaCl solution", Journal of Applied Physics, 1973, 44, pp. 3118-3121.
Heaton, N. J. et al., "High Resolution Bound-Fluid, Free Fluid and Total Porosity with Fast NMR Logging", Transactions of the SPWLA 41st Annual Logging Symposium, Dallas, Texas, USA, Paper V, 2000, 14 pages.
Holmes, W. M. et al., "Investigation of two phase flow and phase trapping by secondary imbibition within Fontainebleau sandstone", Magnetic Resonance Imaging, 2003, 21(3-4), pp. 389-391.
Hoult, D. I., "Fast Recovery, High Sensitivity NMR Probe and Preamplifier for Low Frequencies," Review of Scientific Instrumentation, 1979, 50(2), pp. 193-200.
Howe, A. M. et al., "Visualising surfactant enhanced oil recovery", Colloids and Surfaces A: Physicochemical and Engineering Aspects, 2015, 480, pp. 449-461.

(56) References Cited

OTHER PUBLICATIONS

Hubbard, P. S., "Nonexponential Nuclear Magnetic Relaxation by Quadrupole Interactions", Journal of Chemical Physics 1970, 53(3), pp. 985-987.
Hürlimann, M. D. et al. The Diffusion-Spin Relaxation Time Distribution Function as an Experimental Probe to Characterize Fluid Mixtures in Porous Media, The Journal of Chemical Physics, 2002, 117(22), pp. 10223-10232.
Hürlimann, M. D. et al., "Diffusion-Editing: New NMR Measurement of Saturation and Pore Geometry", Transactions of the SPWLA 43rd Annual Logging Symposium, Paper FFF, 2002, 14 pages.
Hürlimann, M. D. et al., "Quantitative Measurement of Two-Dimensional Distribution Functions of Diffusion and Relaxation in Grossly Inhomogeneous Fields", Journal of Magnetic Resonance, 2002, 157(1), pp. 31-42.
Hürlimann, M. D., "Optimization of timing in the Carr-Purcell-Meiboom-Gill sequence", Magnetic Resonance Imaging, 2001, 19(3-4), pp. 375-378.
Hürlimann, M. D. et al., "Spin Dynamics of Carr-Purcell-Meiboom-Gill-like Sequences in Grossly Inhomogenous B0 and B1 Fields and Application to NMR Well Logging" Journal of Magnetic Resoanance, 2000, 143, pp. 120-135.
Hussain, R. et al., "Monitoring water transport in sandstone using flow propagators: A quantitative comparison of nuclear magnetic resonance measurement with lattice Boltzmann and pore network simulations", Advances in Water Resources, 2013, 60, pp. 64-74.
Hutchison, J. M. S. et al., "A whole-body NMR imaging machine", Journal of Physics E: Scientific Instruments, 1980, 13, pp. 947-955.
Jaccard, G. et al., "Multiple-quantum NMR Spectroscopy of S=3/2 spins in isotropic phase: A new probe for multiexponential relaxation", Journal of Chemical Physics 1986, 85, pp. 6282-6293.
Johann, P. et al., "Reservoir Geophysics in Brazilian Ppre-Salt Oilfields", OTC 23681 presented at the Offshore Technology Conference, Houston, Texas, USA, 2012, 10 pages.
Johns, M. L. et al., "Using MR Techniques to Probe Permeability Reduction in Rock Cores", AIChE Journal, 2003, 49(5), pp. 1076-1084.
Leverett, M. C., "Capillary Behavior in Porous Solids", Transactions AIME 1941, 142(1), pp. 152-169.
Looyestijn, W. J. et al., "Wettability-Index Determination by Nuclear Magnetic Resonance", SPE Reservoir Evaluation & Engineering, 2006, 9(2), pp. 146-153.
Looyestijn, W. J., "Wettability index determination from NMR logs", Petrophysics, 2008, 49, pp. 130-145.
Machado, V. et al., "Carbonate Petrophysics in Wells Drilled with Oil-Base Mud", presented at the SPWLA 52nd Annual Logging Symposium, Colorado Springs, Colorado, USA, 2011, 10 pages.
Majors, P. et al., "NMR Imaging of Immiscible Displacements in Porous Media", SPE-30557, SPE Formation Evaluation, 1977, 12(3), pp. 164-169.
McLachlan, A. D., "Line widths of electron resonance spectra in solution", Proceedings of the Royal Society of London, 1964, A280, pp. 271-288.
Minh, C. et al., "2D-NMR Applications in Unconventional Reservoirs", SPE 161578, presented at the SPE Canadian Unconventional Resources Conference, Calgary, Alberta, Canada, 2012, 17 pages.
Mitchell, J. et al., "A rapid measurement of flow propagators in porous rocks", Journal of Magnetic Resonance, 2008, 191, pp. 267-272.
Mitchell, J. et al., "Contributed Review: Nuclear magnetic resonance core analysis at 0.3 T", Review of Scientific Instruments, 2014, 85, pp. 111502: 17 pages.
Mitchell, J. et al., "Determining NMR flow propagator moments in porous rocks without the influence of relaxation", Journal of Magnetic Resonance, 2008, 193, pp. 218-225.
Mitchell, J. et al., "Low-field permanent magnets for industrial process and quality control", Progress in Nuclear Magnetic Resonance Spectroscopy, 2014, 76, pp. 1-60.
Mitchell, J. et al., "Magnetic resonance imaging in laboratory petrophysical core analysis", Physics Reports, 2013, 526(3), pp. 165-225.
Mitchell, J. et al., "Mapping oil saturation distribution in a limestone plug with low-field magnetic resonance", Journal of Petroleum Science and Engineering, 2013, 108, pp. 14-21.
Mitchell, J. et al., "Numerical estimation of relaxation and diffusion distributions in two dimensions", Progress in Nuclear Magnetic Resonance Spectroscopy, 2012, 62, pp. 34-50.
Mitchell, J. et al., "Quantitative In-Situ Enhanced Oil Recovery Monitoring Using Magnetic Resonance", Transport in Porous Media, 2012, 94, pp. 683-706.
Mitchell, J. et al., "Quantitative Remaining Oil Interpretation Using Magnetic Resonance: From the Laboratory to the Pilot", SPE 154704, presented at the SPE EOR Conference at Oil and Gas West Asia, Muscat, Oman, 2012, 11 pages.
Mitchell, J. et al., "Real-time oil-saturation monitoring in rock cores with low-field NMR", Journal of Magnetic Resonance, 2015, 256, pp. 34-42.
Mitchell, J. et al., Magnetic Resonance Imaging of Chemical EOR in Core to Complement Field Pilot Studies, SCA Conference Paper No. 24, presented at the International Symposium of the Society of Core Analysts, Aberdeen, Scotland, United Kingdom, 2012, 12 pages.
Petrov, O. V., et al., "T2 distribution mapping profiles with phase-encode MRI", Journal of Magnetic Resonance, 2011, 209, pp. 39-46.
Picard, G. et al., "Method for modeling transport of particles in realistic porous netowrks: Application to the computation of NMR flow propagators", Physical Review E, 2007, 75, pp. 066311: 8 pages.
Price, W. S. et al., "Correlation of Viscosity and Conductance with 23NA+ NMR T1 Measurements", Bulletin of the Chemical Society of Japan, 1990, 63(10), pp. 2961-2965.
Rauschhuber, M. et al., "Determination of Saturation Profiles via Low-field NMR Imaging" CSC Conference Paper No. 9, 2009, presented at the International Symposium of the Society of Core Analysts, Noordwijk, The Netherlands, 12 pages.
Rijniers, L. A. et al., "Experimental Evidence of Crystallization Pressure inside Porous Media", Physical Review Letters, 2005, 94, 075503: 4 pages.
Rijniers, L. A. et al., "Sodium NMR relaxation in porous materials", Journal of Magnetic Resonance, 2004, 167, pp. 25-30.
Salathiel, R. A., "Oil Recovery by Surface Film Drainage in Mixed-Wettability Rocks," Journal of Petroleum Technology, 1973, 25(10), pp. 1216-1224.
Scheven, U. M. et al., "A cumulant analysis for non-Gaussian displacement distributions in Newtonian and non-Newtonian flows through porous media", Magnetic Resonance Imaging, 2007, 25, pp. 513-516.
Scheven, U. M. et al., "NMR-propagator measurements in porous media in the presence of surface relaxation and internal fields" Magnetic Resonance Imaging, 2005, 23, pp. 363-365.
Scheven, U. M. et al., "Quantitative nuclear magnetic resonance measurements of preasymptotic dispersion in flow through porous media", Physics of Fluids, 2005, 17, 117107, 7 pages.
Singer, P. M. et al., "Low magnetic fields for flow propagators in permeable rocks", Journal of Magnetic Resonance, 2006, 183, pp. 167-177.
Song, Y-Q. et al., "T1-T2 Correlation Spectra Obtained Using a Fast Two-Dimensional Laplace Inversion", Journal of Magnetic Resonance, 2002, 154(2), pp. 261-268.
Song, Y. Q., "Recent Progress of Nuclear Magnetic Resonance Applications in Sandstones and Carbonate Rocks", Vadose Zone Journal, 2010, 9, pp. 828-834.
Sorbie, K. S. et al., "A Proposed Pore-Scale Mechanism for How Low Salinity Waterflooding Works", SPE 129833 presented at the SPE Improved Oil Recovery Symposium, Tulsa, Oklahoma, USA, 2010.
Straley, C. et al., "NMR in Partially Saturated rocks: laboratory insights on free fluid index and comparison with borehole logs", The Log Analyst, 1995, pp. 40-56.

(56) References Cited

OTHER PUBLICATIONS

Straley, C., et al., "Core Analysis by Low Field NMR", SCA Conference Paper 04, 1994, pp. 43-56.

Tutunjian, P. N. et al., "Nuclear Magnetic Resonance Imaging of Sodium-23 in Cores", The Log Analyst, 1993, 34(3), pp. 11-19.

Van Der Zwaag, C. H. et al., "NMR response of non-reservoir fluids in sandstone and chalk", Magnetic Resoanance Imaging, 2001, 19, pp. 543-545.

Van Der Zwaag, C. H. et al., "Potential Effects of Current and Future Drilling Fluid Systems on Core Analysis", SCA conference Paper No. 16, 2000, 14 pages.

Van Der Zwaag, C. H., et al., "Application of NMR and CT Analytical Methods to Assess the Formation Damage Potential of Drilling Fluids", CA Conference Paper No. 13, 1998.

Venkataramanan, L. et al., "Solving Fredholm integrals of the First Kind with Tensor Product Structure in 2 and 2.5 Dimensions", IEEE Transactions on Signal Processing, 2002, 50(5), pp. 1017-1026.

Washburn, K. E. et al., "Imaging of multiphase fluid saturation within a porous material via sodium NMR", Journal of Magnetic Resonance, 2010, 202(1), pp. 122-126.

Wilson, J. D., "Statistical approach to the solution of first kind integral-equations arising in the study of materials and their properties", Journal of Materials Science, 1992, 27, pp. 3911-3924.

Withjack, E. M. et al., "The Role of X-Ray Computed Tomography in Core Analysis", SPE 83467 presented at the SPE Western Regional/AAPG Pacific Section Joint Meeting, Long Beach, California, USA, 2003, 12 pages.

Woessner, D. E., "NMR Relaxation of Spin-3/2 Nuclei: Effects of Structure, Order, and Dynamics in Aqueous Heterogeneous Systems", Concepts in Magnetic Resonance, 2001, 13(5), pp. 294-325.

Zhang, Y. et al., "Waterflood Performance by Injection of Brine with Different Salinity for Reservoir Cores", SPE 109849 presented at the SPE Annual Technical Conference and Exhibition, Anaheim, California, USA, 2007, 12 pages.

Zhao, W. et al., "Characterization of singe-phase flow through carbonate rocks: quantitative comparison of NMR flow propagator measurements with a realistic pore network model", Transport in Porous Media, 2010, 81, pp. 305-315.

Zhou, X. et al., "Interrelationship of Wettability, Initial Water Saturation, Aging Time, and Oil Recovery by Spontaneous Imbibition and Waterflooding", SPE/DOE 35436 presented at the SPE/DOE Tenth Symposium on Improved Oil Recovery, Tulsa, Oklahoma, USA, 1996, pp. 325-339.

Zielinski, L. et al., "Restricted Diffusion Effects in Saturation Estimates from 2D Diffusion-Relaxation NMR Maps", SPE13484, presented at the 2010 Annual Technical Conference and Exhibition, Florence, Italy, 8 pages.

International Search Report and Written Opinion issued in International Patent application PCT/US2017/050010 dated Dec. 7, 2018, 15 pages.

International Preliminary Report on Patentability issued in International Patent application PCT/US2017/050010 dated Mar. 5, 2019, 11 pages.

* cited by examiner

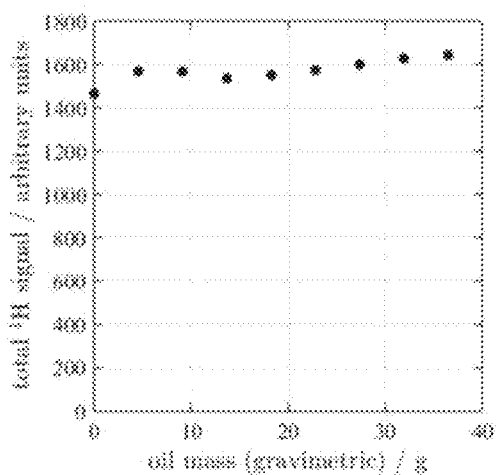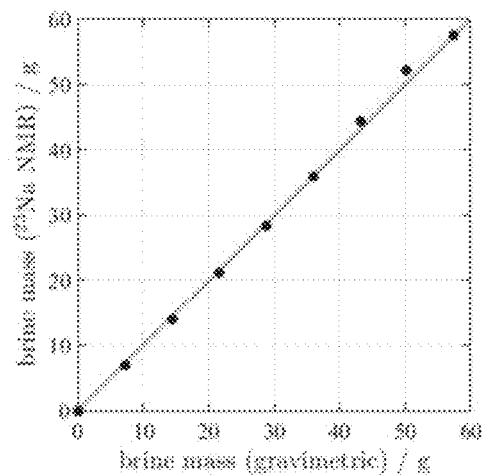
FIG. 2A        FIG. 2B
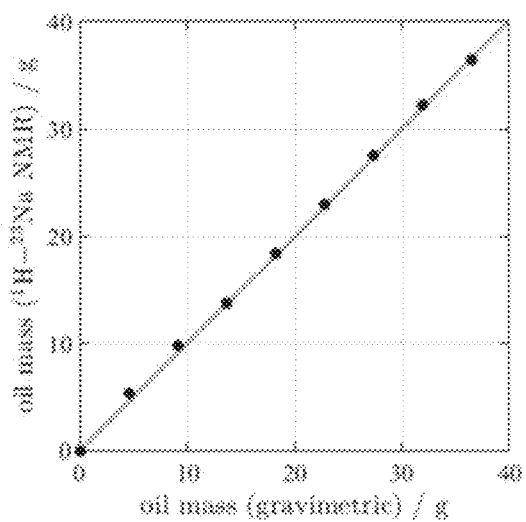
FIG. 2C
FIG. 2

METHODS FOR INTERPRETING NMR DATA

CROSS-REFERENCE TO RELATED APPLICATION

This application claims the benefit of U.S. Provisional Application No. 62/383,242, filed Sep. 2, 2016.

BACKGROUND

This section is intended to introduce the reader to various aspects of art that may be related to various aspects of the presently described embodiments. This discussion is believed to be helpful in providing the reader with background information to facilitate a better understanding of the various aspects of the described embodiments. Accordingly, it should be understood that these statements are to be read in this light and not as admissions of prior art.

The present disclosure relates to methods for interpreting nuclear magnetic resonance (NMR) data. In particular, but not by way of limitation, this disclosure relates to relates to interpretation of NMR data by simultaneously detecting more than one resonant nucleus.

Spatially resolved measurements have been applied to monitoring oil recovery from small rock samples in the laboratory, enabling, for example, rapid screening of enhanced oil recovery (EOR) chemicals (surfactants, polymers). Low-field 1H (proton) NMR is conventionally used for these studies to (a) provide consistent physics of measurement to downhole tools and (b) minimize the effect of magnetic susceptibility contrast on the measurements. NMR has a significant advantage over X-ray computed tomography (CT) in these measurements: the ability to discriminate fluid phases (oil, gas, brine) based on inherent properties of the fluids (spin relaxation time, diffusion coefficient). However, there are cases where these inherent fluid-phase contrast mechanisms are insufficient to discriminate the phases, e.g., mud filtrate invasion in pre-salt carbonate formations.

BRIEF SUMMARY

The present disclosure relates to methods for interpreting NMR data based on more than one resonant nucleus, which may include 1H and at least one other resonant nucleus, to determine materials in a sample (including without limitation over time during a process) and for other purposes as will be described. In a first aspect, the present disclosure provides methods to combine dual- or multi-resonance NMR and core analysis (including dynamic processes such as coreflooding) to improve fluid-phase discrimination where conventional methods fail and/or to access petrophysical parameters that cannot be determined by conventional 1H NMR.

In another aspect, the present disclosure provides methods (e.g., relaxation time analysis, diffusion, imaging, flow propagator) for improved interpretation of NMR data acquired from petrophysical samples by simultaneously detecting more than one resonant nucleus without removing the sample from the sensitive volume of the NMR magnet or radio frequency probe.

In embodiments, The NMR signals from multiple resonant nuclei (e.g., 1H, 23Na, 19F, or 1H and 133Cs, etc.) may be acquired sequentially using a dual resonance probe design. In embodiments, one of the resonant nuclei detected may be 1H for comparison to standard single-nucleus NMR core analysis. Switching between acquisitions of different resonant nuclei may be achieved automatically to enable time-efficient measurements of dynamic processes such as corefloods. The detection of resonant nuclei other than 1H provides additional petrophysical information on a sample or dynamic process that cannot be achieved by conventional contrast mechanisms available when measuring a single resonant nucleus.

A sample may comprise a bulk fluid (e.g., crude oil, brine, gas, drilling mud), fluid-saturated rock sample, or portion of an underground reservoir. A dynamic process may comprise flow of fluid through a rock sample, or displacement of one fluid by another fluid flowing through a rock sample. The measurement may be any NMR acquisition technique currently applied routinely to petrophysical samples using low-field NMR spectrometers (e.g., relaxation time, diffusion coefficient, imaging, flow propagator). The detection of multiple resonant nuclei enables robust and quantitative determination of volumes of multiple fluid-phases in the pores of a rock sample (saturation state).

In another aspect, the present disclosure provides methods for robust imaging/analysis of spatial distribution of different fluids (e.g., 1H, 23Na, 19F) within a core or reservoir rock. The NMR data may be acquired and processed in real-time to enable rapid screening of enhanced oil recovery techniques and products (e.g., polymer EOR, low-salinity waterflood) and/or to provide improved interpretation of well-logs. Measurements of resonant nuclei other than 1H may be performed in the laboratory or downhole with a NMR logging tool.

A non-native nucleus may be introduced in order to provide robust fluid-phase sensitivity or additional information on a reservoir formation. In the context of well-logging, a non-native nucleus may be injected and monitored using the concept of the MicroPilot™.

Alternatively, the resonance frequency of a radio frequency (RF) probe could be switched for detection of different nuclei. Alternatively, the field strength of a magnet could be switched (e.g., using a "cryogen-free" superconducting magnet) such that the resonant frequency between different nuclei remains constant. Furthermore, other techniques may be used for measuring multiple resonant nuclei.

In a further aspect, the present disclosure provides a method of analysing quadrupolar relaxation time behavior to extract single values of the quadrupole coupling constant (QCC) and rotational correlation time ($\tau_c$) to provide an interpretation on the geometric environment of sodium nuclei solution in porous materials.

The rotational correlation time distribution may be interpreted as a pore size distribution. The quadrupole coupling constant distribution may be interpreted as a pore size distribution. The rotational correlation time distribution may be used to extract the permeability of the porous media. The quadrupole coupling constant distribution may be used to extract the permeability of the porous media.

The system being studied may be a subsurface formation containing a brine of sodium ions. The system may be measured by means of a logging tool lowered into the formation, or formation material extracted from the reservoir. The system being studied may be a porous construction material (stone, concrete, brick) where transport of salt influences the in-service performance. In embodiments, measurements of QCC-$\tau_c$ correlations may be used to provide information on the state and environment of sodium-salts in solution.

QCC and $\tau_c$ values may be obtained by least-squares fitting of Equations (1) and (2) below to separate (1D) $T_1$ and $T_2$ relaxation time data. It is the divergence of $T_{2a}$ and $T_{2b}$ at long correlation times that provides a robust determination of $\tau_c$. The ratio $T_{2a}/T_{2b}$ may provide an alternative interpretation without the need to extract an explicit correlation time. QCC is defined by the absolute $T_1$ or $T_2$ values, and can be determined from a measure of either.

Outside the motional narrowing regime, $T_1$ and $T_2$ become frequency dependent (although QCC and $\tau_c$ do not), so additional information may be obtained by comparing the relaxation behavior at different magnetic field strengths. For example, changes in QCC and $\tau_c$ indicate the sodium nuclei are encountering the pore surface (otherwise bulk relaxation behavior would be observed). Modifications of the spectral density function (see Equation (8) below) may be used to provide improved analysis of complex dynamics inside porous media and/or to enable inference of the fluid-pore interactions.

The methods herein described here may be applied to other quadrupolar nuclei including without limitation lithium.

BRIEF DESCRIPTION OF THE DRAWINGS

For a detailed description of embodiments of the present disclosure, reference will now be made to the accompanying drawings in which:

FIG. 2 (including FIGS. 2A through 2C) shows an example of dual resonance detection in accordance with one or more embodiments of the present disclosure;

DETAILED DESCRIPTION

Figure 1:
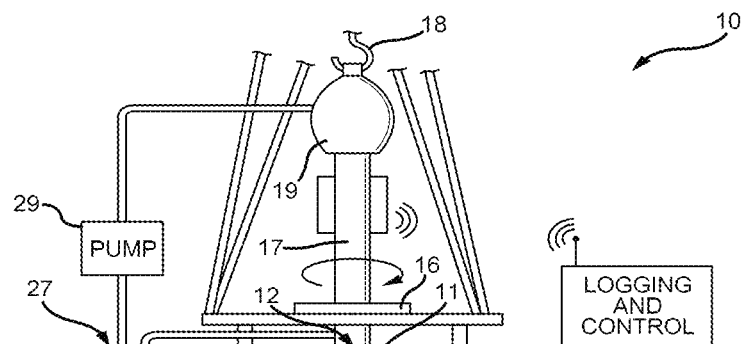
FIG. 1 schematically illustrates an example wellsite system in which one or more embodiments of the present disclosure can be employed.

Reference will now be made in detail to embodiments, examples of which are illustrated in the accompanying drawings and figures. In the following detailed description, numerous specific details are set forth in order to provide a thorough understanding of the subject matter herein. However, it will be apparent to one of ordinary skill in the art that the subject matter may be practiced without these specific details. In other instances, well-known methods, procedures, components, and systems have not been described in detail so as not to unnecessarily obscure aspects of the embodiments.

This discussion is directed to various embodiments of the disclosure. The drawing figures are not necessarily to scale. Certain features of the embodiments may be shown exaggerated in scale or in somewhat schematic form, and some details of conventional elements may not be shown in the interest of clarity and conciseness. Although one or more of these embodiments may be preferred, the embodiments disclosed should not be interpreted, or otherwise used, as limiting the scope of the disclosure, including the claims. It is to be fully recognized that the different teachings of the embodiments discussed may be employed separately or in any suitable combination to produce desired results. In addition, one skilled in the art will understand that the description has broad application and that the discussion of any embodiment is meant only to be exemplary of that embodiment, and not intended to intimate that the scope of the disclosure, including the claims, is limited to that embodiment.

The terminology used in the description of the disclosure herein is for the purpose of describing particular embodiments only and is not intended to be limiting of the subject matter. When introducing elements of various embodiments of the present disclosure and claims, the articles "a," "an," "the," and "said" are intended to mean that there are one or more of the elements. The term "and/or" as used herein refers to and encompasses any and all possible combinations of one or more of the associated listed items. The terms "comprising," "including," and "having" are used in an open-ended fashion, and thus should be interpreted to mean "including, but not limited to . . . ."

As used herein, the term "if" may be construed to mean "when" or "upon" or "in response to determining" or "in response to detecting," depending on the context. Similarly, the phrase "if it is determined" or "if (a stated condition or event) is detected" may be construed to mean "upon determining" or "in response to determining" or "upon detecting (the stated condition or event)" or "in response to detecting (the stated condition or event)," depending on the context.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Certain terms are used throughout the description and claims to refer to particular features or components. As one skilled in the art will appreciate, different persons may refer to the same feature or component by different names. This document does not intend to distinguish between components or features that differ in name but not function, unless specifically stated.

Referring now to the drawings, FIG. 1 schematically illustrates an example wellsite system in which the methods of the present disclosure can be employed. The wellsite can be onshore or offshore. In this exemplary system, a borehole 11 is formed in subsurface formations by rotary drilling in a manner that is well known. Embodiments of the present disclosure can also use directional drilling, as will be described hereinafter. As shown in FIG. 1, a drill string 12 is suspended within the borehole 11 and has a bottomhole assembly 100 which includes a drill bit 105 at its lower end. The surface system includes platform and derrick assembly 10 positioned over the borehole 11, the assembly 10 including a rotary table 16, kelly 17, hook 18 and rotary swivel 19. The drill string 12 is rotated by the rotary table 16, energized by means not shown, which engages the kelly 17 at the upper end of the drill string. The drill string 12 is suspended from a hook 18, attached to a traveling block (also not shown), through the kelly 17 and a rotary swivel 19 which permits rotation of the drill string relative to the hook. As is known, a top drive system could alternatively be used.

The example surface system may further include drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 105, and then circulates upwardly through the annulus region between the outside of the drill string and the wall of the borehole, as indicated by the directional arrows 9. In this known manner, the drilling fluid lubricates the drill bit 105 and carries formation cuttings up to the surface as it is returned to the pit 27 for recirculation.

As shown, the bottomhole assembly 100 may include for non-limiting example a logging-while-drilling (LWD) module 120, a measuring-while-drilling (MWD) module 130, a rotary steerable system and motor, and drill bit 105. The LWD module 120 is housed in a special type of drill collar, as is known in the art, and may contain one or a plurality of known types of logging tools. It will also be understood that more than one LWD and/or MWD module can be employed, e.g. as represented at 120A. (References, throughout, to a module at the position of 120 can alternatively mean a module at the position of 120A or other positions as well.) As depicted, the LWD module includes capabilities for measuring, processing, and storing information, as well as for communicating with the surface equipment.

The NMR methods of the present disclosure may be used in a laboratory, at a rig-site or as part of a well-logging service.

In embodiments of the present disclosure, a dual resonance RF probe is used to detect NMR signals from (at least) two resonant nuclei in a sample of relevance, for example to the oil industry. One of these resonant nuclei is likely to be 1H, and the measurement and interpretation of these data will be consistent with standard methods. The use of a dual or multi-resonance probe (or alternative method described below) to detect NMR signals from two or more resonant nuclei in the same sample allows dynamic processes such as coreflooding to be monitored continuously without the requirement to move the sample between magnets or RF probes.

The measurement of nuclei other than 1H can provide robust fluid-phase discrimination where the conventional contrast mechanism of 1H relaxation time or diffusion coefficient are insufficient to distinguish the fluid phases. For example, cations such as 23Na or 7Li will be present only in the aqueous phase, providing a unique tracer for brine. Fluorinated oils can be introduced so that 19F can provide a unique tracer for oil. If the NMR signal amplitude (or other measureable property) can be calibrated in terms of the number of nuclear spins, the data will provide in situ quantitative measures of liquid mass (and volume if the density is known).

Detection of nuclei other than 1H can provide access to petrophysical properties not usually available in NMR core analysis. For example, nuclei with very long relaxation times, e.g., 13C and 133Cs, can be used to measure NMR flow propagators over much longer times (providing access to the slower interstitial velocities) than can be achieved with 1H. Similarly, these slow-relaxing nuclei can be used to estimate the degree of diffusive coupling between small and large pores in carbonate formations where 1H relaxation again places a limit on the maximum time-scale for the measurement. The NMR flow propagator measurement has been suggested as a calibrator or validator for Digital Rock™. Other nuclei, such as 23Na or 19F, can be used to measure multiphase propagators as an alternative to chemical shift at low field.

Detection of multiple nuclei can provide an alternative measure of pore size. For example, sodium undergoes enhanced relaxation on contact with a pore wall. Therefore, a relaxation time distribution can be converted into a pore size.

The applications highlighted above focus primarily on laboratory core analysis. However, other resonant nuclei could be detected with logging tools, enabling direct detection of drilling mud invasion (for example) and improved oil/brine discrimination downhole. Injection of solutions containing other nuclei into the near-wellbore formation for enhanced petrophysical interpretation could be achieved using the MicroPilot™ concept.

Dual resonance acquisitions for improved quantification of saturation states during coreflood are demonstrated using examples of 1H/23Na detection. A dual resonance radio frequency (RF) probe was built in the UK based on the concepts taught in D. I. Hoult, Fast recovery, high sensitivity NMR probe and preamplifier for low frequencies, Rev. Sci. Instrum. 50 (1979) 193-200. This probe was installed on a 0.3 T magnet. This instrument is suitable for core analysis applications, notably for carbonate formations with minimal magnetic susceptibility contrast and unconventional (shale) samples.

Example 1: Brine-Decane Emulsions

FIG. 2 shows an example of dual resonance detection in accordance with one or more embodiments of the present disclosure. In particular, FIG. 2 shows the example of dual resonance detection of 1H/23Na for quantification of oil and brine in emulsion samples in the forms of total 1H signal as a function of oil fraction (FIG. 2A), brine mass determined by 23Na (FIG. 2B), and oil mass determined by difference in 1H and 23Na measurements (FIG. 2C).

A series of emulsion samples were generated ranging from 100% brine to 100% decane. The ratio of oil and brine was varied linearly between these two extremes. Standard 1H contrast mechanisms of $T_2$ relaxation time or diffusion coefficient are unable to distinguish between oil and brine in these samples (see below for further details). To quantify the mass of oil and brine in each sample, a combination of 1H and 23Na measurements were used. The total 1H and 23Na signal amplitudes were obtained for each sample. Using the extreme cases of 100% brine and 100% decane, the following calibrations were obtained: $C_w$—1H signal per unit mass water; $C_s$—23Na signal per unit mass salt (at known concentration); and $C_o$—1H signal per unit mass decane.

A scaling constant $C_{ws}$ was also obtained, which converts the 23Na signal amplitude into an equivalent 1H signal per unit mass brine, such that $C_w = C_s/C_{ws}$. The following information was obtained from the NMR signal amplitudes of each sample:

Mass of salt $m_s = S_{Na}/C_s$, where $S_{Na}$ is the 23Na signal amplitude.

Mass of water $m_w = S_w/C_w$, where $S_w = S_{Na}/(C_s/C_{ws})$ is the 1H signal amplitude due to water predicted using the 23Na signal amplitude.

Mass of oil $m_o = (S_H - S_w)/C_o$ where $S_H$ is the total 1H signal amplitude.

These masses can then be converted into volumes if the densities of the liquids are known. Therefore, by measuring the total 1H signal, see FIG. 2A, and the total 23Na signal, it is possible to predict the fraction of 1H signal arising from the water, see FIG. 2B, assuming the sodium concentration is known, and hence determine the fraction of 1H arising from oil as the difference between the total 1H signal (measured by 1H NMR) and the estimated 1H water signal (measured by 23Na NMR), see FIG. 2C. The measurements of brine mass and oil mass determined by dual resonance NMR of the present disclosure are in good agreement with the known masses of liquid determined by conventional gravimetric assay.

For this method to work, it is necessary to know the sodium content of the brine. It is possible to estimate sodium concentration from the 23Na $T_1$ or $T_2$ relaxation times or diffusion coefficient, although it is necessary to have knowledge of the brine chemistry to quantitatively determine the sodium concentration from these data. Non-NMR based measurements are usually available to determine brine chemistry; these methods are known to those skilled in the art.

Example 2: Oil Recovery Monitoring

Figure 3A:
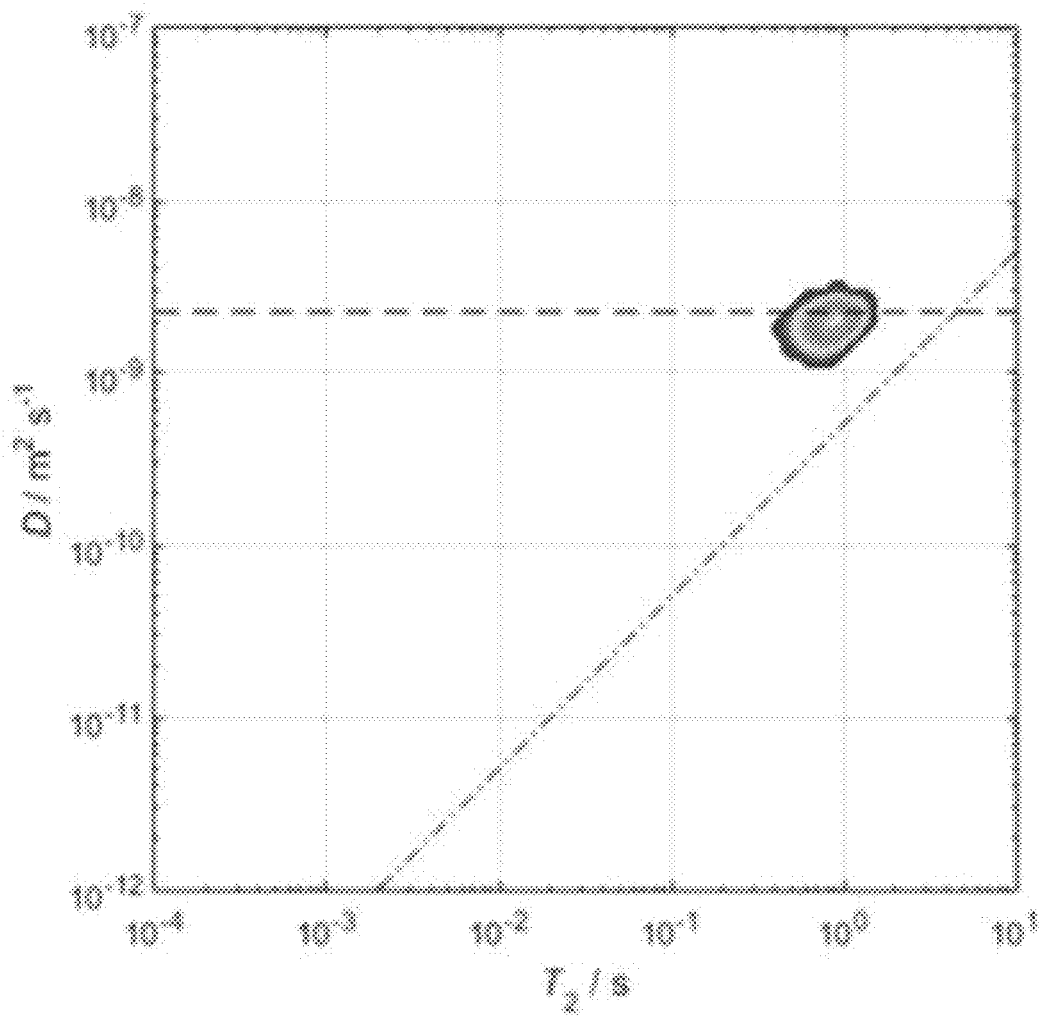
FIGS. 3A through 3C show an example of dual resonance detection in accordance with one or more embodiments of the present disclosure.
Figure 3B:
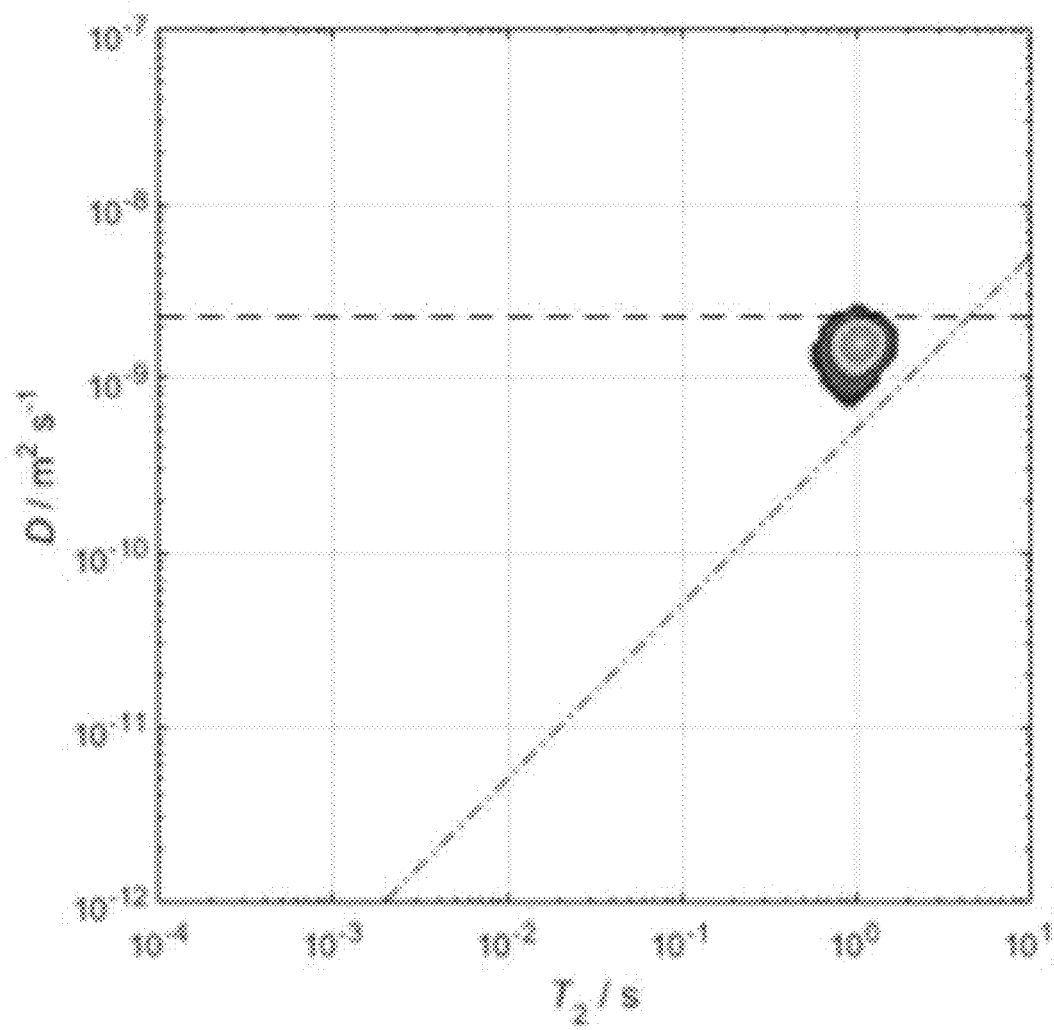
Figure 3C:
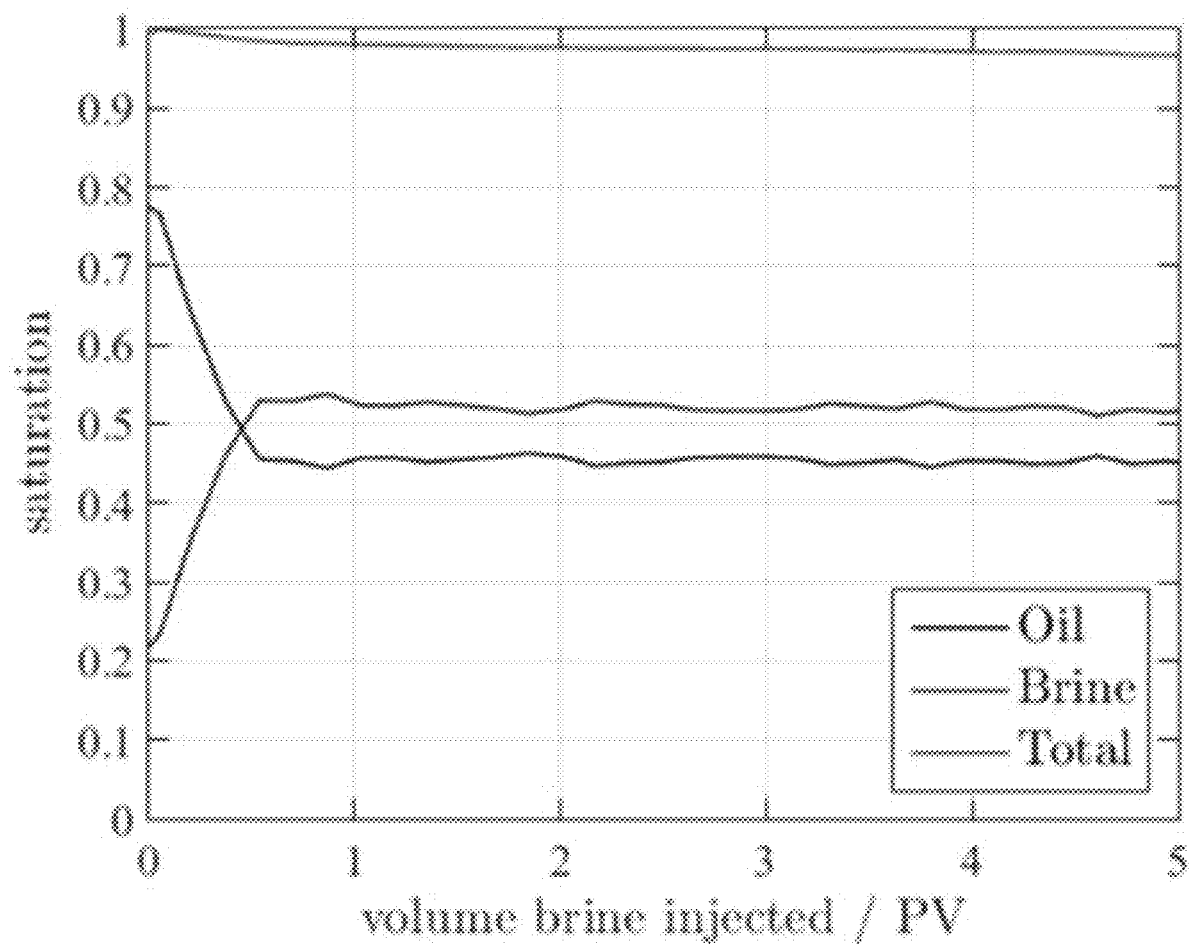

The methods described in "Example 1" above are now demonstrated in FIGS. 3A through 3C in an example of dual resonance detection in a rock plug in accordance with one or more embodiments of the present disclosure. In particular, FIGS. 3A through 3C show coreflood monitoring of decane displaced by high-salinity brine in a Bentheimer sandstone plug. Conventional 1H D-$T_2$ correlation plots are unable to distinguish between the cases of fully brine saturated (FIG. 3A) and 80% oil saturated (FIG. 3B). However, using 1H and 23Na detection, the oil and brine saturations can be monitored during the coreflood. The variation in saturation state as a function of time (volume brine injected) is shown in FIG. 3C.

The rock, a Bentheimer sandstone, was initially saturated with a high-salinity brine. The rock was mounted in a NMR-compatible rock core holder; details of the ErgoTech core holder are given in Tutunjian, P. N., Vinegar, H. J., Ferris, J. A., 1993. Nuclear magnetic resonance imaging of sodium-23 in cores. The Log Analyst May-June, 11-19.

Decane was injected into the rock at a high flow rate to displace the brine and create an initial oil saturation of $S_o = 80\%$. Conventional 1H D-$T_2$ correlations were obtained before and after injection of the oil, see FIGS. 3A and 3B, respectively. Due to the similarity between the relaxation times and diffusion coefficients of decane and water, these standard contrast mechanisms fail to discriminate between the fluid phases.

High-salinity brine was injected into the rock plug at a constant volumetric flow rate. 1H and 23Na signal amplitudes were measured continuously during the coreflood. The 1H and 23Na acquisitions were interleaved to improve the temporal resolution of the experiment. As the resonance frequencies of the two nuclei are so different, the two measurements do not interfere with each other. To measure quantitative signal amplitudes, it is necessary to allow the spins sufficient time to return to their equilibrium state in the magnet field. For 1H nuclei, the recovery time is typically around 10 s, whereas 23Na nuclei recover in less than 1 s. Therefore, it is possible to acquire and sum multiple repeat 23Na scans whilst waiting for the 1H nuclei to recover after a single scan. As the 23Na measurement is inherently less sensitive (lower frequency, fewer nuclei available to detect), summing repeat scans improves the signal-to-noise ratio (SNR) of the data.

The calibration constants and method detailed in Example 1 (above) were used to determine the fractions of oil and brine in the rock plug during the coreflood. The result is given in FIG. 3C where the remaining oil is quantified.

Prior to the introduction of dual resonance NMR of the present disclosure, it was necessary to substitute all aqueous-phase liquids with D2O—so that the 1H signal corresponds only to oil—when using light oils like decane in corefloods. However, this prior method was undesirable because (i) D2O is expensive and (ii) no in situ information is available on the brine content.

Example 3: $T_2$-Cutoff Calibration

In well-logging and laboratory corefloods, it is usual to determine the fractions of oil and brine using a $T_2$-cutoff to distinguish the contributions of each fluid-phase to the measured $T_2$ distributions. However, determining where the $T_2$-cutoff should be positioned is not always straightforward. In well-logs, the $T_2$-cutoff is usually chosen based on supporting evidence from other logs. In the laboratory, it may be determined by measuring a core plug saturated with known volumes of brine and oil. Calibration of the $T_2$-cutoff can still be ambiguous, especially if the $T_2$ distributions corresponding to oil and brine overlap significantly.

Dual resonance NMR of the present disclosure provides quantitative assays of oil and brine in core plugs, as demonstrated in Examples 1 and 2. Therefore, $T_2$-cutoffs can be determined more robustly in the laboratory, see FIG. 4, with support from dual resonance measurements. The calibrated $T_2$-cutoffs can then be applied to well-logs to improve interpretation.

Figure 4:
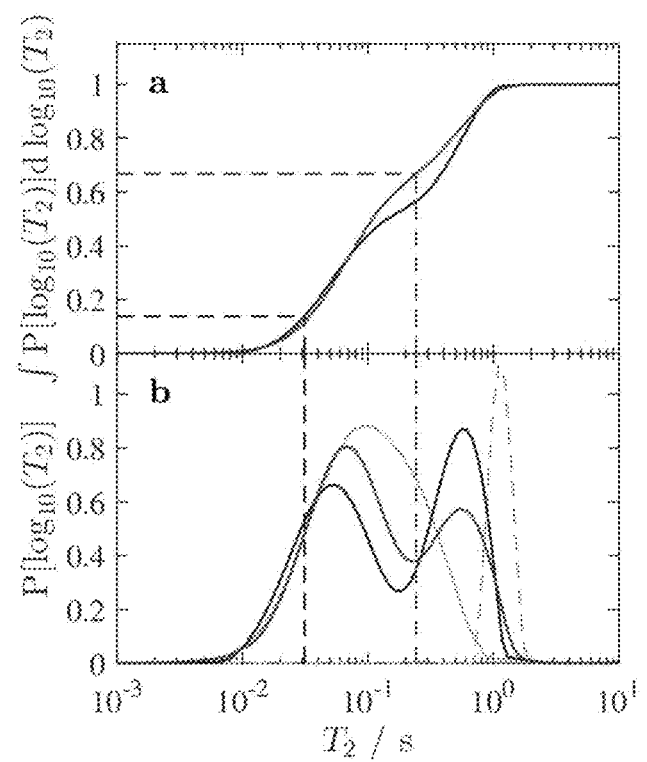
FIG. 4 shows an example of dual resonance detection in accordance with one or more embodiments of the present disclosure.

An example of $T_2$-cutoffs obtained for brine and light oil in a limestone plug at different saturation states are given in FIG. 4. In particular, FIG. 4 demonstrates $T_2$-cutoff calibration. The fractions of brine and light oil (L2 Indopol polybutene, manufactured by INEOS) in an Estaillades limestone plug were determined using 1H and 23Na for the cases of $S_w$=15% (blue) and $S_w$=65% (red). The fraction of signal amplitude corresponding to the water is correlated to $T_2$ using the cumulative intregal of the $T_2$ distribution (a). The $T_2$-cutoffs are overlaid on the $T_2$ distributions in (b), with the distributions for Sw=100% (solid grey line) and bulk L2 oil (dashed grey line) included. Note that due to the overlap in the $T_2$ distributions of the oil and brine in the rock, the selection of a $T_2$-cutoff is not straightforward and requires calibration.

The calibrated $T_2$-cutoffs obtained at different oil saturations, along with the overall shape of the $T_2$ distributions, could be used to improve the interpretation of well logs, where additional information on the saturation state is unavailable.

Example 4: Lo-Sal Coreflood Monitoring

Figure 5:
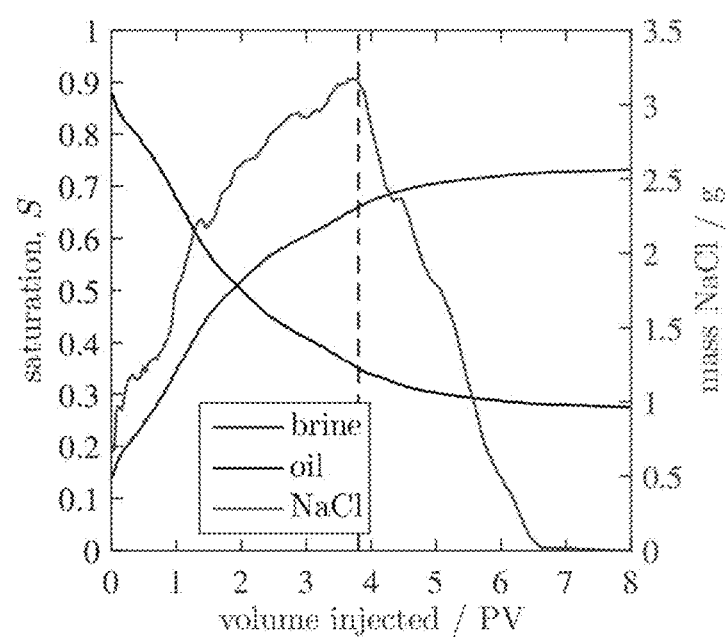
FIG. 5 shows an example of dual resonance detection in accordance with one or more embodiments of the present disclosure.

Another example shows a combined 1H and 23Na measurement to monitor changes in both oil/brine saturation and salinity (sodium-salt content) during a low-salinity (Lo-Sal) coreflood. Lo-Sal waterflooding is a form of EOR, although the exact mechanism by which the change in salinity mobilizes additional oil is not well understood. The ability to monitor both the in situ oil saturation (with 1H NMR) and the salt content (with 23Na NMR) can provide new insights into the recovery mechanisms of Lo-Sal water flooding. For example, spatially resolved measurements will show whether the additional recovery of oil due to low-salinity brine is uniform along the core-plug or associated only with, say, a capillary end effect. An example of monitoring both oil saturation and salt content during a low-salinity coreflood is given in FIG. 5. In particular, FIG. 5 shows displacement of L2 oil from Estaillades limestone by (i) high-salinity brine and (ii) low-salinity brine. The vertical dashed black line indicates the switch from high to low salinity brine. The oil and brine saturations (left-hand axis) were determined by conventional 1H NMR. The mass of NaCl present (right-hand axis) was monitored by 23Na NMR.

Detection of resonant nuclei other than 1H can be implemented alongside conventional low-field NMR measurements. In the context of laboratory SCAL, a dual resonance NMR probe would be used to detect signal from 1H and at least one other nucleus (e.g., 19F or 23Na) during a coreflood experiment. The combination of the two or more measurements enables robust fluid-phase discrimination and hence provides a time-resolved measure of saturation state (fraction of pore space occupied by oil or brine). The standard suite of low-field 1H NMR measurements (e.g., total signal amplitude, relaxation time, diffusion coefficient, and imaging) can be applied to the other nuclei. For example, a one-dimensional image of salt distribution can be obtained by 23Na imaging.

Figure 6:
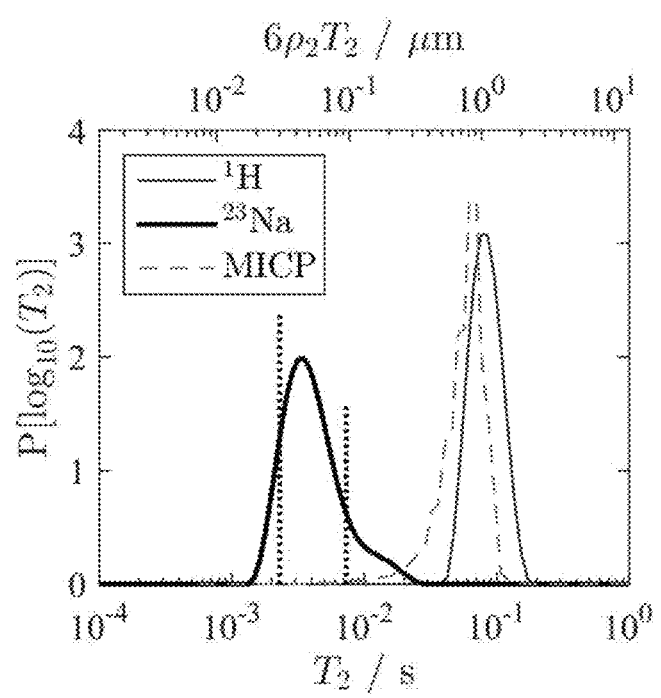
FIG. 6 shows an example of dual resonance detection in accordance with one or more embodiments of the present disclosure.

As described below, some embodiments of the present disclosure address interpretation of sodium relaxation at pore surfaces. An interpretation for spin-3/2 nuclear relaxation in porous materials is provided. The incomparability of $T_2$ distributions obtained for 1H and 23Na in a monodispersed porous medium is illustrated in FIG. 6. In particular, FIG. 6 shows comparison of 1H and 23Na $T_2$ distributions in Stevns Klint chalk saturated with 5M NaCl brine. SNR≈100 for both NMR measurements. The 1H $T_2$ distribution reflects the pore size distribution, and is consistent with the mercury intrusion capillary pressure (MICP) pore throat size distribution, scaled to relaxation time with surface relaxivity $\rho_2$=2.17 μm s$^{-1}$ for 1H. The 23Na $T_2$ distribution is characterized by two relaxation time components, $T_{2a}$=2.3 ms and $T_{2b}$=7.3 ms (vertical dotted lines obtained by least-squares fit) (plus bulk liquid signal at $T_2$=37 ms), and does not reflect the pore size.

There are four Zeeman eigenstates associated with the quadrupole spin-3/2 sodium nucleus, resulting in two different decay probabilities for excited spins. In general, the longitudinal relaxation rates are $$\frac{1}{T_{1a}} = Aj_1, \quad \frac{1}{T_{1b}} = Aj_2, \qquad \text{Equation (1)}$$

and the transverse relaxation rates are $$\frac{1}{T_{2a}} = \frac{1}{2}A[j_0 + j_1], \quad \frac{1}{T_{2b}} = \frac{1}{2}A[j_1 + j_2], \qquad \text{Equation (2)}$$

where the spectral densities for pure quadrupole relaxation are $$j_n = \frac{\tau_c}{1 + (n\omega_0 \tau_c)^2}, \qquad \text{Equation (3)}$$

$\omega_0$ being the Larmor frequency and $\tau_c$ the rotational correlation time. The pre-factor is $$A = \frac{2}{5}\left(1 + \frac{\theta^2}{3}\right)\pi^2 QCC^2, \qquad \text{Equation (4)}$$

where θ is the asymmetry parameter, with the quadrupole coupling constant $$QCC^2 = \left(\frac{eQ}{\hbar}\right)^2 \langle (eq(t))^2 \rangle, \qquad \text{Equation (5)}$$

where h is Planck's constant, eQ is the (constant) nuclear quadrupole moment and eq(t) is the time-dependent electric field gradient at the nucleus. The observed recovery of longitudinal magnetization is $$M(t) = 1 - \left[\frac{1}{5}\exp\left\{-\frac{t}{T_{1a}}\right\} + \frac{4}{5}\exp\left\{-\frac{t}{T_{1b}}\right\}\right], \qquad \text{Equation (6)}$$

and the decay of transverse magnetization is $$M(t) = \frac{3}{5}\exp\left\{-\frac{t}{T_{2a}}\right\} + \frac{2}{5}\exp\left\{-\frac{t}{T_{2b}}\right\}. \qquad \text{Equation (7)}$$

Figure 7:
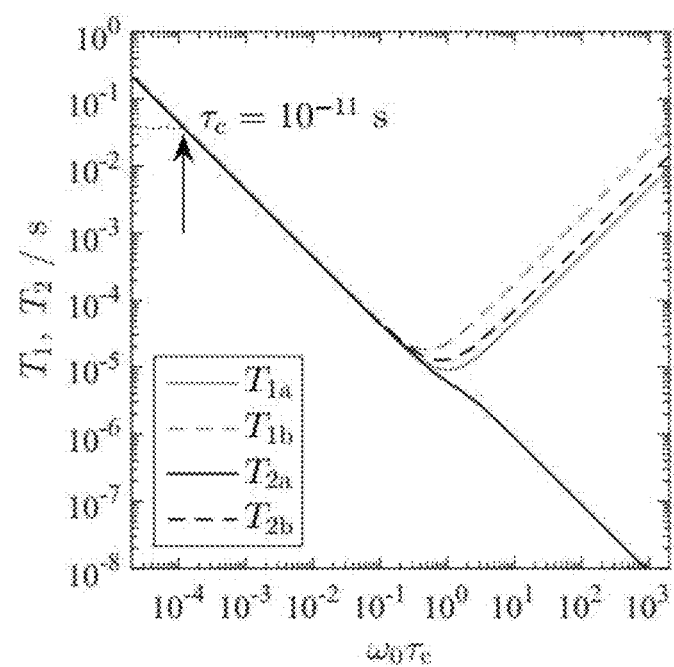
FIG. 7 shows relaxation times as a function of rotational correlation time in accordance with one or more embodiments of the present disclosure.

The relaxation times as a function of rotational correlation time is illustrated in FIG. 7. In particular, FIG. 7 shows variation of 23Na relaxation times with $\tau_c$. The quadrupole coupling constant is fixed at QCC=1.1 MHz and $\omega_0$=2.2× 107 rad s$^{-1}$ ($\nu_0$=3.4 MHz). The arrow indicates the theoretical correlation time for saturated NaCl solution at ambient conditions.

Under the condition of motional narrowing (bulk ionic solutions) the relaxation rates collapse to a single value $$\frac{1}{T_1} = \frac{1}{T_2} = \frac{2}{5}\pi^2\left(1 + \frac{\theta^2}{3}\right)QCC^2\tau_c. \qquad \text{Equation (8)}$$

We assume θ=0 for the symmetric hydration sphere of a sodium ion. In Equation (8) the rotational correlation time is defined by the solution viscosity η as $$\tau_c = \frac{4\pi\eta r_0^3}{3kT}, \qquad \text{Equation (9)}$$

where $r_0$=0.201 nm is the Stokes radius of the sodium ion and kT is the Boltzmann temperature. Note that the relaxation rates for 23Na in bulk solution are independent of Larmor frequency.

Correlated $T_1$-$T_2$ relaxation time data are determined using the saturation-recovery-CPMG (Carr-Purcell-Meiboom-Gill) pulse sequence that is known to those skilled in the art. It is usual to treat these data as an ill-posed inverse problem that is solved numerically to generate a 2D $T_1$-$T_2$ correlation. A kernel function describes the expected form of the data as $$k(t_1, nt_e, T_1, T_2) = \left[1 - \exp\left\{-\frac{t_1}{T_1}\right\}\right]\left[\exp\left\{-\frac{nt_e}{T_2}\right\}\right]. \qquad \text{Equation (10)}$$

The actual 2D magnetization decay is described by $$\frac{M(t_1, nt_e)}{M(0, 0)} = \left[1 - \left(\frac{1}{5}\exp\left\{-\frac{t_1}{T_{1a}}\right\} + \frac{4}{5}\exp\left\{-\frac{t_1}{T_{1b}}\right\}\right)\right] \times \left[\frac{3}{5}\exp\left\{-\frac{nt_e}{T_{2a}}\right\} + \frac{2}{5}\exp\left\{-\frac{nt_e}{T_{2b}}\right\}\right]. \qquad \text{Equation (11)}$$

Figure 8:
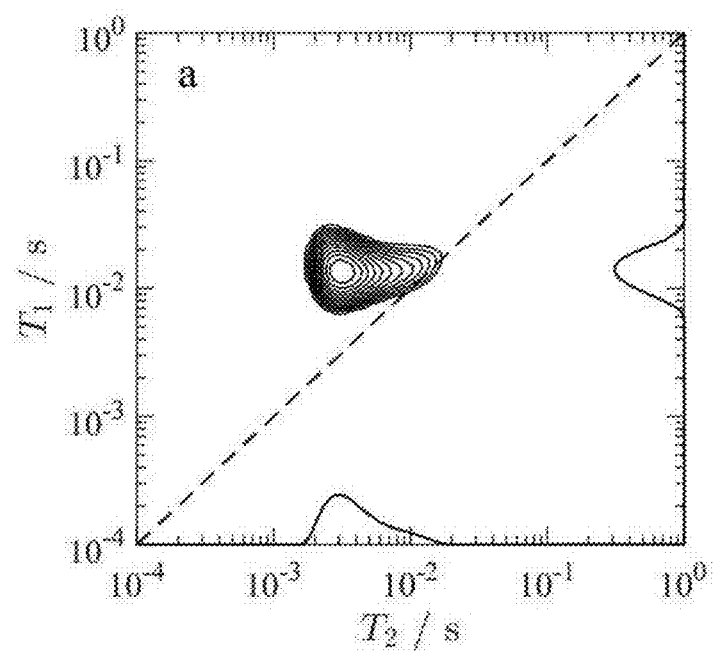
FIG. 8 shows T1-T2 23Na correlation obtained for 5M NaCl brine in Stevns Klint chalk in accordance with one or more embodiments of the present disclosure.

However, the 2D inversion cannot fit the "a" and "b" components separately, and a broad distribution encompassing all four relaxation times is observed instead, see FIG. 8. In particular, FIG. 8 shows $T_1$-$T_2$ 23Na correlation obtained for 5M NaCl brine in Stevns Klint chalk. The dashed line indicates $T_1$=$T_2$. Marginal distributions are shown for clarity, the $T_2$ dimension is consistent with the 1D distribution shown in FIG. 2 Four relaxation time components are present, $T_{1a}$, $T_{1b}$, $T_{2a}$, $T_{2b}$, according to Equations (6) and (7). Smoothing applied by the inversion algorithm means the separate components are not resolved.

A kernel function of the present disclosure can be used to extract values for the underlying parameters that define the relaxation time behavior of the quadrupolar sodium nucleus. This new kernel has the form $$k(t_1, nt_e, QCC, \tau_c) = \qquad \text{Equation (12)}$$
$$\left[1 - \left(\frac{1}{5}\exp\{-Aj_1 t_1\} + \frac{4}{5}\exp\{-Aj_2 t_1\}\right)\right] \times$$
$$\left[\frac{3}{5}\exp\left\{-\frac{1}{2}A(j_0 + j_1)nt_e\right\} + \frac{2}{5}\exp\left\{-\frac{1}{2}A(j_1 + j_2)nt_e\right\}\right],$$

where the fitted parameters are QCC and $\tau_c$, encompassed by A, from Equation (6), and $j_n$, from Equation (7), respectively. As the two dimensions of this inversion are not separable, the method of Venkataramanan et al. cannot be applied.

Figure 9:
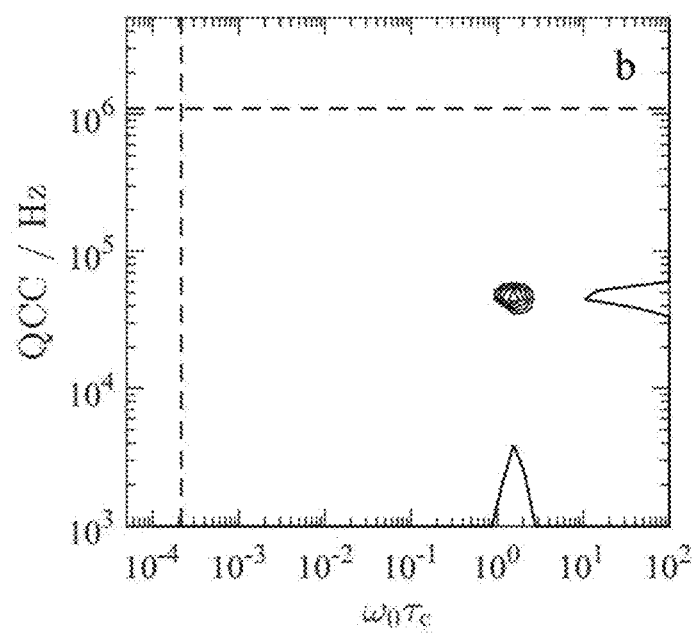
FIG. 9 shows QCC-τc correlation for 5M NaCl brine in Stevns Klint chalk in accordance with one or more embodiments of the present disclosure.

An example QCC-$\tau_c$ correlation is shown in FIG. 9. Note that single values of QCC and $\tau_c$ define the relaxation behavior of the quadrupolar sodium nucleus. In particular, FIG. 9 shows QCC-$\tau_c$ correlation for 5M NaCl brine in Stevns Klint chalk. Marginal distributions are included for clarity. The effective parameter values are QCC=46 kHz and $\tau_c$=70 ns. The dashed lines indicated the bulk brine values of QCC=1.1 MHz and $\tau_c$=10 ps. Note that single values of QCC and $\tau_c$ define the relaxation behavior of the quadrupolar sodium nucleus.

The observed QCC and $\tau_c$ values observed in the porous material are significantly removed from values measured in other rotationally hindered systems, so these measured values are considered to be "effective" in the sense that they reflect an average behavior between sodium ions at the surface (rotationally hindered motion) and sodium ions diffusing in the bulk solution in the middle of the pores. The two populations are in "fast exchange" on the time-scale of the measurement, resulting in single QCC and $\tau_c$ values. The $\tau_c$ distribution is expected to reflect the pore size distribution through a scaling parameter (equivalent to the surface relaxivity parameter $\rho_2$ that scales $T_2$ to pore size).

Figure 10:
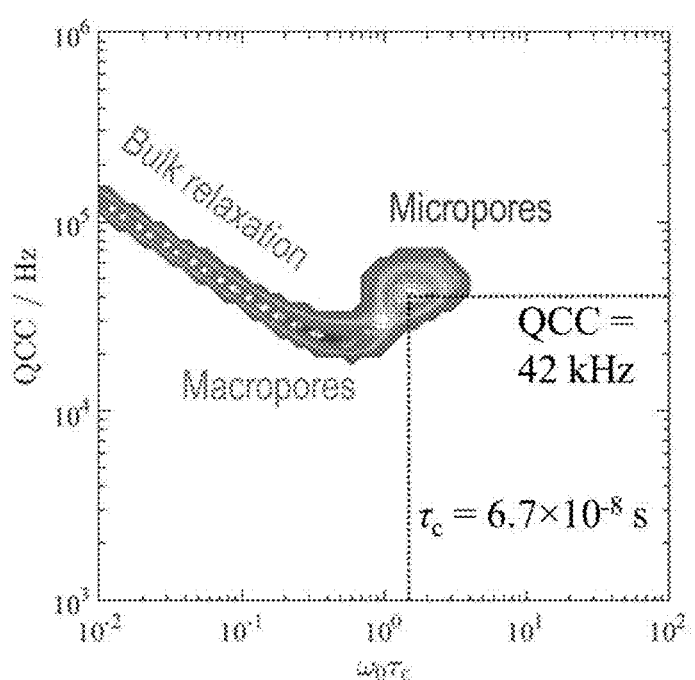
FIG. 10 shows QCC-$\tau_c$ correlation for 5M NaCl brine in Estaillades limestone in accordance with one or more embodiments of the present disclosure.

A possible interpretation relates the QCC and $\tau_c$ values to pore size. An example is given in FIG. 10 for a bimodal pore size rock (Estaillades limestone). In particular, FIG. 10 shows QCC-$\tau_c$ correlation for 5M NaCl brine in Estaillades limestone. The rock structure contains two modal pore sizes, identified here as "micropores" (pore body size ~1 μm) and "macropores" (pore body size >10 μm). Regions of the QCC-$\tau_c$ correlation have been associated with brine in these structures in the figure. A well-defined peak is observed in the QCC-$\tau_c$ correlation at QCC=42 kHz and $\tau_c$=67 ns, associated with sodium spins that are rotationally hindered by adsorption on the rock surface. Although these spins can desorb, and the effective QCC and $\tau_c$ values are an average of surface-adsorbed and free-diffusing spins, there is clearly a population of spins that spend the majority of the time on the pore surface. This well-defined peak in the QCC-$\tau_c$ correlation is therefore associated with the "micropores" (high surface-to-volume ratio). A less well-defined peak is observed at $\omega_0\tau_c$<1, which stretches into a long line on the left hand side of the figure. This signal component is associated with sodium spins that are mostly undergoing free-diffusion, but occasionally see a pore surface, such that $T_1$=$T_2$ but the relaxation times are reduced from those of the bulk NaCl solution. This region of the QCC-$\tau_c$ correlation is therefore associated with the "macropores" (low surface-to-volume ratio).

Access to 23Na through the methods of the present disclosure may be used in a variety of applications. For example, salt crystallization is known to damage construction materials such as stone and concrete, and sodium content is a quality control indicator in the food industry. However, no one has addressed interpretation of sodium relaxation at the pore surface. Rijniers et al. attempted to apply the theory of Brownstein and Tarr to sodium relaxation in order to extract a pore size information in L. A. Rijniers, P. C. M. M. Magusin, H. P. Huinink, L. Pel, K. Kopinga, J. Magn. Reson. 167 (2004) 25-30. However, the interpretation was incorrect, as the "fast diffusion" model for 1H spin relaxation in a pore cannot be extended, unaltered, to 23Na. There are four Zeeman eigenstates associated with the quadrupole spin-3/2 sodium nucleus, resulting in two different decay probabilities for excited spins. Outside the motional narrowing regime, the probabilities for the inner and satellite transitions differ, leading to biexponential relaxation for this quadrupolar nucleus.

To analyze and interpret 23Na measurements in porous media, the present disclosure teaches use of a novel kernel function in the usual two-dimensional (2D) inversion of relaxation time data. When measuring 23Na nuclei with hindered rotational motion, as found for sodium ions adsorbed on a pore surface, the usual longitudinal ($T_1$) and transverse ($T_2$) relaxation times are unhelpful and do not reflect the pore size distribution of the porous material. Instead, the 2D relaxation time is inverted to probe the fundamental parameters of quadrupolar relaxation, namely the quadrupole coupling constant (QCC) and rotational correlation time ($\tau_c$), to form a novel QCC-$\tau_c$ correlation. In an ideal material with a monodispersed pore size distribution (e.g., microporous chalk), the usual 23Na $T_1$-$T_2$ correlation contains four relaxation time components ($T_{1a}$, $T_{1b}$, $T_{2a}$, $T_{2b}$), whereas the QCC-$\tau_c$ correlation exhibits unique single (effective) values of QCC and $\tau_c$ that can be interpreted in terms of the pore size/throat distribution, pore geometry, and the like.

The main commercial competitor to NMR for special core analysis (SCAL) and oil recovery monitoring is X-ray. Although X-ray does not suffer the same restrictions on sample volume as NMR, it is necessary to include doping agents to provide fluid-phase discrimination. The addition of doping agents is not ideal as these can alter the complex interfacial fluid properties, especially in the presence of say, surfactants, and also potentially interact with the rock surface. X-rays can provide spatial resolution, although this capability is rarely offered in commercial core laboratories.

Oil recovery can also be monitored by effluent analysis, although this requires precision measurements of mass and calibration of flow pipe volumes. Ensuring the capture of volatile gases is challenging, and no spatial information is available. This is an indirect measurement of the saturation state and involves complicated analysis to infer the behavior of fluids in the rock sample.

There are situations in which the inherent fluid-contrast mechanisms exploited by NMR fail. Examples include a mix of light oil (or high GOR) and brine, where the relaxation times and diffusion coefficients of both phases are comparable. Another example is oil-based mud (OBM) filtrate invasion in pre-salt carbonate formations that complicates interpretation of the NMR signal.

The detection of carefully chosen NMR-sensitive nuclei allows completely robust fluid-phase separation and hence accurate determination of the saturation state. An example is the detection of 23Na as a tracer for brine, as sodium is found only in the aqueous phase. The standard experiments available with 1H NMR can be implemented with other nuclei, including measurements of total signal amplitude, relaxation times, diffusion coefficient, and imaging.

The use of a multiple-resonance NMR probe allows measurements of two (or more) nuclei to be interleaved (e.g., 133Cs, 1H, 23Na for monitoring mud filtrate invasion), so there is no significant increase in acquisition time compared to a standard 1H experiment.

Nuclei other than 1H exhibit a variety of properties that might prove useful in core analysis. For example, 133Cs has very long relaxation times, making it potentially useful in the flow propagator experiment or T2-T2 exchange experiment.

The use of a multiple-resonance probe (or related concept) in embodiments of the present disclosure means the sample can be measured continuously during dynamic processes such as coreflooding without the requirement to move the sample between different magnets or probes. The present disclosure provides an improved system over: single-nucleus NMR, because it provides more robust fluid discrimination and independent and simultaneous imaging of oil and water; X-ray, because no dopants are required, it has built in phase sensitivity, it measures fluid properties as well, and it achieves quantitative volumetrics, measurements vs. monitoring; and gravimetric effluent analysis, because it is faster, automatable, more accurate and it provides fluid distribution inside the core.

Commercial applications of sodium NMR include logging and core/drill cuttings analysis e.g. robust discrimination of brine. NMR measurements of sodium may also be useful in the following contexts: emulsion droplet sizing in oil-based drilling fluids when the aqueous-phase contains a sodium-salt; monitoring water floods of reservoirs when the sodium-salt content of the injection and connate water is different; monitoring of low-salinity brine injection in reservoirs or core plugs for improved (enhanced) oil recovery; monitoring of salt transport in building materials (brick, stone, concrete) where dissolution and re-crystallization of salt can result in structural damage; and measuring sodium-salt concentration in production water for quality control and safe disposal regulations.

Machine-readable instructions of modules described above are loaded for execution on a processor. A processor can include a microprocessor, microcontroller, processor module or subsystem, programmable integrated circuit, programmable gate array, graphics processing unit, or another control or computing device.

Data and instructions are stored in respective storage devices, which are implemented as one or multiple computer-readable or machine-readable storage media. The storage media include different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

Reference throughout this specification to "one embodiment," "an embodiment," or similar language means that a particular feature, structure, or characteristic described in connection with the embodiment may be included in at least one embodiment of the present disclosure. Thus, appearances of the phrases "in one embodiment," "in an embodiment," and similar language throughout this specification may, but do not necessarily, all refer to the same embodiment.

The foregoing outlines features of several embodiments and sets forth numerous details so that those skilled in the art may better understand the aspects of the present disclosure. Those skilled in the art should appreciate that the present disclosure may provide a basis for designing or modifying other processes and structures for carrying out the same purposes and/or achieving the same advantages of the embodiments introduced herein.

Although the present disclosure has been described with respect to specific details, it is not intended that such details should be regarded as limitations on the scope of the invention, except to the extent that they are included in the accompanying claims.

The invention claimed is:

1. A method of interpreting multi-nuclear nuclear magnetic resonance (NMR) data comprising:
    obtaining an industry standard sample for analysis;
    measuring two or more selected NMR signal amplitudes in the sample each corresponding to a resonant nuclei, wherein one of the measured NMR signal amplitudes corresponding to 1H; and
    determining the masses of two or more selected substances in the sample corresponding the two or more selected NMR signal amplitudes, wherein a mass of salt is determined from a 23Na signal amplitude, a mass of water is determined from the 1H signal amplitude due to water predicted using the 23Na signal amplitude, and a mass of oil is determined from the 1H signal amplitude.

2. The method of claim 1 wherein the measuring is performed using a multi-resonant radio frequency probe of a size to accommodate the industry standard sample.

3. The method of claim 1 wherein the measuring is performed using a magnetic field switching system, wherein the field switching is implemented via variable-current iron or air-cored electromagnet, and a field is switched such that a detection frequency for a second and a subsequent nuclei matches the detection frequency for a first nucleus at a first field.

4. The method of claim 1 wherein a near-simultaneous acquisition is achieved by automated interleaving of acquisition sequences.

5. The method of claim 1 wherein measuring two or more selected NMR signals is performed by a downhole logging tool.

6. The method of claim 1 wherein the distribution of two or more resonant nuclei is spatially imaged in 1 or 2 or 3 dimensions.

7. The method of claim 1 further comprising:
    yielding quantitative volumetric interpretation of the substances containing the resonant nuclei.

8. The method of claim 1, wherein the measuring is performed as a function of time during a time-varying process in the sample.

9. The method of claim 8, wherein the time-varying process is displacement of oil from a petrophysical rock sample where the displacing fluid is brine with or without additional chemicals or a gas or a foam or a supercritical fluid.

10. The method of claim 9, wherein the time-varying process is displacement of or dissolution in aqueous phases in a subsurface rock sample where the displacing fluid is carbon dioxide.

11. The method of claim 9, wherein the time-varying process is transport of salt in construction materials and a resonant nucleus is Cs133.

12. The method of claim 9, wherein the time-varying process is transport of the resonant nucleus from an oil-well drilling fluid to a formation sample or potential phase separation in oil-well drilling fluid.

13. The method of claim 1, further comprising:
    calibrating the two or more selected NMR signal amplitudes.

14. The method of claim 13, wherein calibrating the two or more selected NMR signal amplitudes includes obtaining a 1H signal per unit mass water and a 23Na signal per unit mass salt.

15. The method of claim 13, wherein calibrating the two or more selected NMR signal amplitudes includes applying a scaling constant that converts a 23Na signal amplitude into an equivalent 1H signal per mass brine.

16. The method of claim 1, wherein the mass of salt is determined using the equation $m_s = S_{Na}/C_s$, where $m_s$ is the mass of salt, $S_{Na}$ is the 23Na signal amplitude, and $C_s$ is a salt calibration constant at a known concentration.

17. The method of claim 1, wherein the mass of water is determined using the equation $m_s = S_w/C_w$, where $m_s$ is the mass of water, $S_w$ is the 1H signal amplitude due to water predicted using the 23Na signal amplitude, and $C_w$ is a water calibration constant.

18. The method of claim 17, wherein $C_w$ is obtained by using a salt calibration constant at a known concentration and a scaling constant that converts a 23Na signal amplitude into an equivalent 1H signal per mass brine.

19. The method of claim 1, wherein the mass of oil is determined using the equation $m_o = (S_H - S_w)/C_o$, where $m_o$ is the mass of oil, $S_H$ is a total 1H signal amplitude, $S_w$ is the 1H signal amplitude due to water predicted using the 23Na signal amplitude, and $C_o$ is a 1H signal per unit mass oil.

20. The method of claim 1, wherein determining the masses of two or more selected substances in the sample corresponding the two or more selected NMR signal amplitudes includes:
    measuring a total 1H signal and a total 23Na signal;
    predicting a fraction of the 1H signal arising from the water; and
    determining a fraction of the 1H signal arising from oil as a difference between the total 1H signal and an estimated 1H water signal obtained from the total 23Na signal.

* * * * *